(12) United States Patent
Frąckowiak et al.

(10) Patent No.: US 9,243,008 B1
(45) Date of Patent: Jan. 26, 2016

(54) FUNCTIONALIZED UNSATURATED DERIVATIVES OF (DIMETHYLVINYLGERMOXY)-HEPTASUBSTITUTED SILSESQUIOXANES AND THE METHOD OF THEIR SYNTHESIS

(71) Applicant: ADAM MICKIEWICZ UNIVERSITY, Poznań (PL)

(72) Inventors: Dawid Frąckowiak, Poznań (PL); Patrycja Żak, Poznań (PL); Bogdan Marciniec, Swarzędz (PL)

(73) Assignee: Adam Mickiewicz University, Poznan (PL)

( * ) Notice: Subject to any disclaimer, the term of this patent is extended or adjusted under 35 U.S.C. 154(b) by 0 days.

(21) Appl. No.: 14/677,663

(22) Filed: Apr. 2, 2015

(30) Foreign Application Priority Data

Feb. 11, 2015 (PL) .......................................... 411196

(51) Int. Cl.
*C07F 7/30* (2006.01)
*C07F 7/21* (2006.01)

(52) U.S. Cl.
CPC ........................................ *C07F 7/21* (2013.01)

(58) Field of Classification Search
CPC ..................................... C07F 7/21; C07F 7/30
USPC .................................................... 556/10, 460
See application file for complete search history.

(56) References Cited

U.S. PATENT DOCUMENTS

| | | | | |
|---|---|---|---|---|
| 7,662,308 B2* | 2/2010 | Jeganathan | .......... | C08G 77/045 106/31.64 |
| 7,947,848 B2* | 5/2011 | Ohrlein | ..................... | C07F 7/21 556/460 |
| 8,299,283 B2* | 10/2012 | Chujo | ................... | A61K 49/124 534/15 |
| 9,012,673 B1* | 4/2015 | Mabry | ................. | C08G 77/045 556/460 |
| 9,018,400 B2* | 4/2015 | Marciniec | ................. | C07F 7/21 549/214 |
| 2005/0215807 A1* | 9/2005 | Morimoto | .............. | C08G 77/04 556/460 |
| 2010/0222503 A1* | 9/2010 | Laine | ................... | C08G 77/045 524/588 |
| 2013/0158282 A1* | 6/2013 | Christiansen | ............ | B01J 31/24 556/460 |
| 2014/0275445 A1* | 9/2014 | Yamanaka | .............. | C08L 83/04 525/476 |

OTHER PUBLICATIONS

Frackowiak et al., Organometallics, vol. 34, No. 16, pp. 3950-3958 (2015).*

* cited by examiner

*Primary Examiner* — Porfirio Nazario Gonzalez
(74) *Attorney, Agent, or Firm* — Oliff PLC

(57) ABSTRACT

The invention relates to new functionalized unsaturated derivatives of (dimethylvinylgermoxy)heptasubstituted silsesquioxanes of the general formula 1, (1)

and the method in which:
R are the same and represent linear and branched $C_2$ to $C_8$ alkyl groups, or cyclopentyl and cyclohexyl groups, or phenyl groups
R' represents an unsubstituted aryl group containing between 1 and 2 rings or an aryl group substituted in any position in the ring.
The invention also relates to the method of synthesis of functionalized unsaturated derivatives of (dimethylvinylgermoxy)heptasubstituted silsesquioxanes.

13 Claims, No Drawings

FUNCTIONALIZED UNSATURATED DERIVATIVES OF (DIMETHYLVINYLGERMOXY)-HEPTASUBSTITUTED SILSESQUIOXANES AND THE METHOD OF THEIR SYNTHESIS

The invention relates to new functionalized unsaturated derivatives of (dimethylvinylgermoxy)heptasubstituted silsesquioxanes and the method of their synthesis.

The purpose of the invention was to synthesize molecules of silsesquioxanes having a (dimethylvinylgermoxyl) substituent substituted with an aryl group.

In the first aspect, the invention relates to new functionalized unsaturated derivatives of cage (dimethylvinylgermoxy) heptasubstituted silsesquioxanes of the general formula 1,

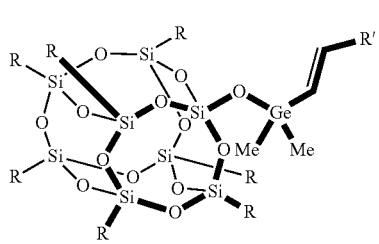

(1)

in which:
R are the same and represent:
  linear and branched $C_2$ to $C_8$ alkyl groups,
  cyclopentyl and cyclohexyl groups,
  phenyl groups,
R' represents:
  an unsubstituted aryl group containing between 1 and 2 rings,
  an aryl group substituted in any position in the ring with one of the following groups:
    a $C_1$ to $C_2$ alkyl group,
    an alkoxyl group containing a $C_1$ to $C_2$ alkyl group,
    a halogen: F, Cl, Br,
    halogenoalkyl which contains a $C_1$ to $C_2$ alkyl group and is completely substituted with the halogen F or Cl.

In the second aspect, the invention relates to the method of synthesis of functionalized unsaturated derivatives of (dimethylvinylgermoxy)heptasubstituted silsesquioxanes containing a vinyl group substituted with an aryl group of the general formula 1,

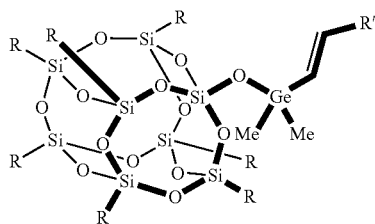

(1)

in which:
R are the same and represent:
  linear and branched $C_2$ to $C_8$ alkyl groups,
  cyclopentyl and cyclohexyl groups,
  phenyl groups,
R' represents:
  an unsubstituted aryl group containing between 1 and 2 rings,
  an aryl group substituted in any position in the ring with one of the following groups:
    a $C_1$ to $C_2$ alkyl group,
    an alkoxyl group containing a $C_1$ to $C_2$ alkyl group,
    a halogen: F, Cl, Br,
    a halogenoalkyl which contains a $C_1$ to $C_2$ alkyl group and is completely substituted with the halogen F or Cl,
the method comprising the reaction of conjugation of (dimethylvinylgermoxy)heptasubstituted silsesquioxanes of the general formula 2,

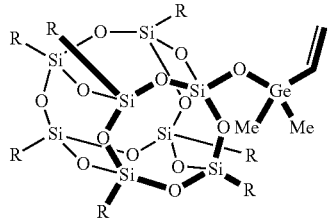

(2)

in which R are the same and represent:
linear and branched $C_2$ to $C_8$ alkyl groups,
cyclopentyl and cyclohexyl groups,
phenyl groups,
with olefins of the general formula 3,

(3)

in which R' represents:
an unsubstituted aryl group containing between 1 and 2 rings,
an aryl group substituted in any position in the ring with one of the following groups:
  a $C_1$ to $C_2$ alkyl group,
  an alkoxyl group containing a $C_1$ to $C_2$ alkyl group,
  a halogen: F, Cl, Br,
  a halogenoalkyl which contains a $C_1$ to $C_2$ alkyl group and is completely substituted with the halogen F or Cl,
in the presence of a ruthenium complex as a catalyst.

The catalyst is the compound of the general formula 4, $$RuHCl(CO)[P(R'')_3]_n \qquad (4)$$

in which n represents 2 or 3, and when n=3, R" represents triphenylphosphine; and when n=2, R" represents tricyclohexylphosphine or triisopropylphosphine.

The catalyst is used in an amount ranging from $1 \times 10^{-3}$ to $1 \times 10^{-1}$ of Ru per 1 mol of (dimethylvinylgermoxy)heptasubstituted silsesquioxane of the formula 2, whereby it is advantageous to use between $0.5 \times 10^{-2}$ and $5 \times 10^{-2}$ mol, and the most advantageous amount is $2 \times 10^{-2}$ mol.

The reaction is advantageously performed with an addition of a copper(I) or (II) salt as a cocatalyst, particularly a copper (I) salt, most advantageously copper(I) chloride in an amount of $10^{-1}$-10 mol of Cu, advantageously 5 mol of Cu per 1 mol of Ru.

The reaction is advantageously carried out in a solvent in an atmosphere of an inert gas in a closed system, whereby it is advantageous to use gas that has been purified of oxygen and moisture. The reactions are carried out at temperatures not exceeding 200° C.

It is necessary to use an excess of olefin in relation to (dimethylvinylgermoxy)heptasubstituted silsesquioxane in order to avoid by-processes. It is advantageous to use an excess of between 1.2 and 3 mol of olefin per 1 mol of (dimethylvinylgermoxy)heptasubstituted silsesquioxane of the formula 1, preferably ca. 1.5.

The reactions are carried out in solvents selected from the group consisting of aromatic organic compounds, advantageously in toluene, xylenes, and most advantageously in toluene.

In the method according to the invention, a reaction vessel is loaded in an atmosphere of an inert gas with an appropriate amount of (dimethylvinylgermoxy)heptasubstituted silsesquioxane, a solvent and alkene. The reaction is carried out at temperatures not lower than 130° C., advantageously above 140° C. Due to the minimum temperature limit the reaction is carried out in solvents with a boiling point above 130° C., and in the case of solvents with lower boiling points it is necessary to use closed systems. It is advantageous to maintain a constant temperature throughout the entire duration of the process. The reaction is carried out over 16-48 hours.

If the reaction is carried out with a cocatalyst, the reagents and the catalyst are the first to be introduced into the system, and only then, after the complete dissolution of the catalyst, the cocatalyst is introduced. The presence of the cocatalyst has a favourable effect on increasing the speed of the reaction and the yield of the obtained product, and on reducing the amount of arising by-products.

Cage (dimethylvinylgermoxy)heptasubstituted silsesquioxanes consist of a silicon-oxygen siloxane core and a dimethylvinylgermoxyl group [OGeMe$_2$(CH=CH$_2$)] bound directly to the silicon atom belonging to the inorganic skeleton.

Functionalized unsaturated derivatives of (dimethylvinylgermoxy)heptasubstituted silsesquioxanes to which the invention relates contain a vinyl group of the dimethylyinylgermoxyl group substituted with different functional groups, which makes the compounds suitable as starting materials for obtaining hybrid materials and as nanofillers in new-generation composite materials. In addition, owing to the presence of the germanium atom in the lateral substituent of the silsesquioxane cage, the compounds exhibit specific optical properties and can have an application for the manufacture of precursors for elements of composite optical materials.

The method according to the invention is presented in examples given below which do not limit the applications of the invention.

The analysis of products was performed with:
the $^1$H and $^{13}$C-NMR spectra were recorded on a Varian Gemini 300 spectrometer at 300 and 75 MHz,
the $^{29}$Si NMR spectra were recorded on a Varian Avance 600 spectrometer at 119.203 MHz, Identification data of acquired compounds are listed in Table 1.

EXAMPLE I

A Schlenk flask with a volume of 10 mL, equipped with a magnetic stirrer and a glass stopper was evacuated in a triple vacuum-gas cycle and then charged in an atmosphere of an inert gas with 0.1 g (1.04×10$^{-4}$ mol) of (dimethylvinylgermoxy)heptaisobutylsilsesquioxane, 2 mL of deoxygenated and dried toluene and 24 μL (2.08×10$^{-4}$ mol) of styrene. The reaction mixture was heated to the boil while constantly stirring, following which a 0.0015 g (2.08×10$^{-6}$ mol) portion of [chlorohydridocarbonylbis(tricyclohexylphosphine)ruthenium(II)] was added to it. The reaction mixture was heated at a temperature of 140° C. for 24 hours. The solvent was then evaporated under vacuum, and the residues were combined with 2 mL of methanol. The solvent was decanted, and the remaining precipitate was washed again with 2 mL of methanol. [Dimethyl(E)-styrylgermoxy]heptaisobutylsilsesquioxane in the form of powder was obtained and dried under vacuum (isolation yield of 88%).

EXAMPLE II

Following the procedure set out in Example I, a reaction was carried out between (dimethylvinylgermoxy)heptaisobutylsilsesquioxane (0.1 g, 1.04×10$^{-4}$ mol), 4-bromostyrene (27 μL, 2.08×10$^{-4}$ mol), toluene (2 mL) and [chlorohydridocarbonylbis(tricyclohexylphosphine)ruthenium(II)] (0.0015 g, 2.08×10$^{-6}$ mol). [(E)-4-bromostyryldimethylgermoxy]heptaisobutylsilsesquioxane in the form of powder was obtained with a yield of 85%.

EXAMPLE III

Following the procedure set out in Example I, a reaction was carried out between (dimethylvinylgermoxy)heptaisobutylsilsesquioxane (0.1 g, 1.04×10$^{-4}$ mol), 4-chlorostyrene (25 μL, 2.08×10$^{-4}$ mol), toluene (2 mL) and [chlorohydridocarbonylbis(tricyclohexylphosphine)ruthenium(II)] (0.0015 g, 2.08×10$^{-6}$ mol). [(E)-4-chlorostyryldimethylgermoxy]heptaisobutylsilsesquioxane in the form of powder was obtained with a yield of 81%.

EXAMPLE IV

Following the procedure set out in Example I, a reaction was carried out between (dimethylvinylgermoxy)heptaisobutylsilsesquioxane (0.1 g, 1.04×10$^{-4}$ mol), 4-trifluoromethylstyrene (31 μL, 2.08×10$^{-4}$ mol), toluene (2 mL) and [chlorohydridocarbonylbis(tricyclohexylphosphine)ruthenium(II)] (0.0015 g, 2.08×10$^{-6}$ mol). [Dimethyl(E)-4-trifluoromethylstyrylgermoxy]heptaisobutylsilsesquioxane in the form of powder was obtained with a yield of 87%.

TABLE 1

EXAMPLE I

| | |
|---|---|
| Name of chemical compound | [Dimethyl(E)-styrylgermoxy]heptaisobutylsilsesquioxane |
| Formula of chemical compound | 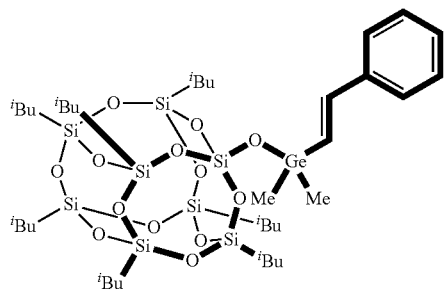 |
| NMR analysis | $^1$NMR (CDCl$_3$, δ, ppm): 0.59 (s, 6H, —Ge(CH$_3$)$_2$—); 0.59-0.65 (m, 14H, CH$_2$); 0.93-0.98 (m, 42H, CH$_3$); 1.80-1.91 (m, 7H, CH); 6.63 (d, 1H, J$_{HH}$ = 18.9 Hz, =CHGe); 6.95 (d, 1H, J$_{HH}$ = 18.9 Hz, =CH—C$_6$H$_5$); 7.12-7.47 (m, 5H, C$_6$H$_5$)<br>$^{13}$C NMR (CDCl$_3$, δ, ppm): 1.00 (—Ge(CH$_3$)$_2$—); 22.45, 22.53 (CH$_2$); 23.80, 23.83 (CH); 25.67 (CH$_3$); 126.55, 127.77, 128.34, 128.51, 144.01 (=CH—C$_6$H$_5$); 206.92 (=CHGe)<br>$^{29}$Si NMR: (CDCl$_3$, δ, ppm): −67.27, −67.90, −108.14 |

EXAMPLE II

| | |
|---|---|
| Name of chemical compound | [(E)-4-bromostyryldimethylgermoxy]heptaisobutylsilsesquioxane |
| Formula of chemical compound | 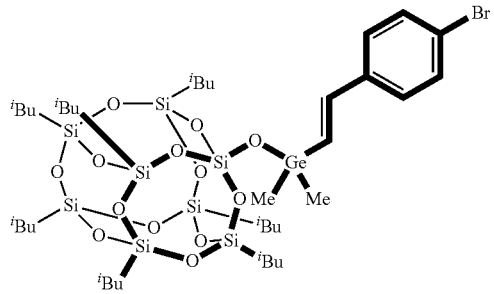 |
| NMR analysis | $^1$NMR (CDCl$_3$, δ, ppm): 0.58 (s, 6H, —Ge(CH$_3$)$_2$—); 0.59-0.65 (m, 14H, CH$_2$); 0.87-1.00 (m, 42H, CH$_3$); 1.78-1.94 (m, 7H, CH); 6.61 (d, 1H, J$_{HH}$ = 18.8 Hz, =CHGe); 7.29-7.33 (m, 2H, C$_6$H$_4$—Br); 7.38 (d, 1H, J$_{HH}$ = 18.8 Hz, =CH—C$_6$H$_4$—Br); 7.52-7.62 (m, 3H, C$_6$H$_4$—Br)<br>$^{13}$C NMR (CDCl$_3$, δ, ppm): 1.00 (—Ge(CH$_3$)$_2$—); 22.47, 22.53 (CH$_2$); 23.81, 23.84 (CH); 25.68 (CH$_3$); 127.03, 127.43, 129.49, 131.63, 142.50 (=CH—C$_6$H$_4$); 206.93 (=CHGe)<br>$^{29}$Si NMR: (CDCl$_3$, δ, ppm): −67.25, −67.90, −108.04 |

EXAMPLE III

| | |
|---|---|
| Name of chemical compound | [(E)-4-chlorostyryldimethylgermoxy]heptaisobutylsilsesquioxane |
| Formula of chemical compound | 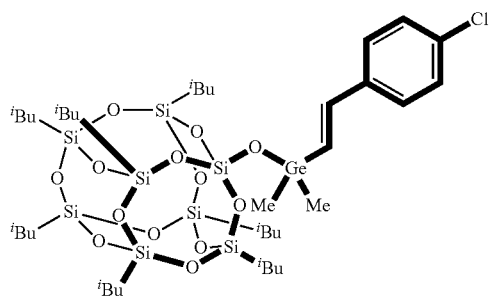 |

TABLE 1-continued

| NMR analysis | $^1$NMR (CDCl$_3$, δ, ppm): 0.54 (s, 6H, —Ge(CH$_3$)$_2$—); 0.56-0.69 (m, 14H, CH$_2$); 0.86-1.08 (m, 42H, CH$_3$); 1.77-1.96 (m, 7H, CH); 6.60 (d, 1H, J$_{HH}$ = 19.1 Hz, =CHGe); 6.90 (d, 1H, J$_{HH}$ = 19.1 Hz, =CH—C$_6$H$_4$—Cl); 7.27-7.46 (m, 4H, C$_6$H$_4$—Cl)<br>$^{13}$C NMR (CDCl$_3$, δ, ppm): 0.96 (—Ge(CH$_3$)$_2$—); 22.41, 22.50 (CH$_2$); 23.77, 23.80 (CH); 25.63, 25.68 (CH$_3$); 127.37, 127.49, 127.70, 134.00, 142.65 (=CH—C$_6$H$_4$—Cl); 206.80 (=CHGe)<br>$^{29}$Si NMR: (CDCl$_3$, δ, ppm): −67.27, −67.89, −107.04 |
|---|---|

EXAMPLE IV

| Name of chemical compound | [Dimethyl(E)-4-trifluoromethylstyrylgermoxy]heptaisobutylsilsesquioxane |
|---|---|
| Formula of chemical compound | 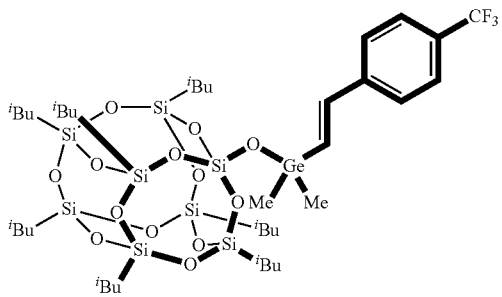 |
| NMR analysis | $^1$NMR (CDCl$_3$, δ, ppm): 0.58 (s, 6H, —Ge(CH$_3$)$_2$—); 0.59-0.66 (m, 14H, CH$_2$); 0.88-1.05 (m, 42H, CH$_3$); 1.78-1.93 (m, 7H, CH); 6.74 (d, 1H, J$_{HH}$ = 18.9 Hz, =CHGe); 6.98 (d, 1H, J$_{HH}$ = 18.9 Hz, =CH—C$_6$H$_4$—CF$_3$); (d, 2H, J$_{HH}$ = 7.9 Hz, C$_6$H$_4$—CF$_3$); 7.59 (d, 2H, J$_{HH}$ = 7.9 Hz, C$_6$H$_4$—CF$_3$)<br>$^{13}$C NMR (CDCl$_3$, δ, ppm): 1.02 (—Ge(CH$_3$)$_2$—), 22.56 (CH$_2$); 23.82, 23.85 (CH); 25.67 (CH$_3$); 25.70 (q, CF$_3$); 126.71, 129.96, 130.22, 131.36, 140.77 (=CH—C$_6$H$_4$—CF$_3$); 142.52 (=CHGe)<br>$^{29}$Si NMR: (CDCl$_3$, δ, ppm): −67.25, −67.86, −105.55 |

The invention claimed is:

1. A functionalized unsaturated derivative of a cage (dimethylvinylgermoxy)heptasubstituted silsesquioxane of the general formula 1,

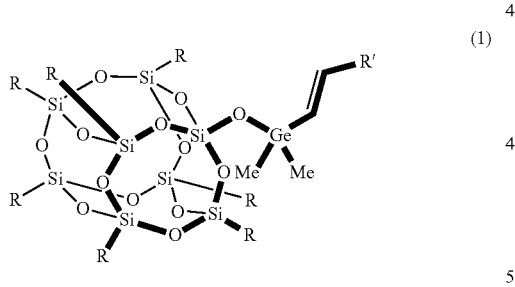

(1)

in which:
R are the same and represent:
linear and branched C$_2$ to C$_8$ alkyl groups,
cyclopentyl and cyclohexyl groups, or
phenyl groups,
R' represents:
an unsubstituted aryl group containing between 1 and 2 rings, or
an aryl group substituted in any position in the ring with one of the following groups:
a C$_1$ to C$_2$ alkyl group,
an alkoxyl group containing a C$_1$ to C$_2$ alkyl group,
a halogen selected from the group consisting of F, Cl, and Br, or
a halogenoalkyl which contains a C$_1$ to C$_2$ alkyl group and is completely substituted with the halogen F or Cl.

2. A method of synthesis of a functionalized unsaturated derivative of a (dimethylvinylgermoxy)heptasubstituted silsesquioxane containing a vinyl group substituted with an aryl group of the general formula 1,

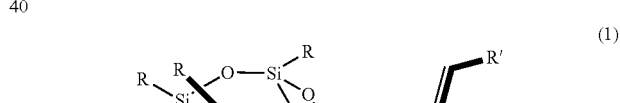

(1)

in which:
R are the same and represent:
linear and branched C$_2$ to C$_8$ alkyl groups,
cyclopentyl and cyclohexyl groups, or
phenyl groups,
R' represents:
an unsubstituted aryl group containing between 1 and 2 rings, or
an aryl group substituted in any position in the ring with one of the following groups:
a C$_1$ to C$_2$ alkyl group,
an alkoxyl group containing a C$_1$ to C$_2$ alkyl group,
a halogen selected from the group consisting of F, Cl, and Br, or
a halogenoalkyl which contains a C$_1$ to C$_2$ alkyl group and is completely substituted with the halogen F or Cl, wherein the method comprises the reaction of conjugation of a (dimethylvinylgermoxy)heptasubstituted silsesquioxane of the general formula 2,

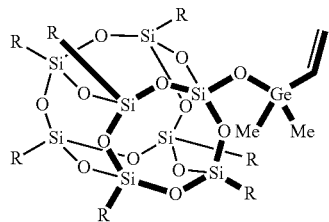

(2)

in which R are the same and represent:

linear and branched $C_2$ to $C_8$ alkyl groups, cyclopentyl and cyclohexyl groups, or phenyl groups, with an olefin of the general formula 3,

(3)

in which R' represents:

an unsubstituted aryl group containing between 1 and 2 rings, or an aryl group substituted in any position in the ring with one of the following groups:

a $C_1$ to $C_2$ alkyl group, an alkoxyl group containing a $C_1$ to $C_2$ alkyl group, a halogen selected from the group consisting of F, Cl, and Br, or a halogenoalkyl which contains a $C_1$ to $C_2$ alkyl group and is completely substituted with the halogen F or Cl, in the presence of a catalyst in the form of a ruthenium complex of the general formula 4,

(4)

in which n represents 2 or 3, and when n=3, R″ represents triphenylphosphine, and when n=2, R″ represents tricyclohexylphosphine or triisopropylphosphine, whereby the reaction is carried out at a temperature not lower than 130° C.

3. The method, as claimed in claim 2, wherein the catalyst is used in an amount from $1\times10^{-3}$ to $1\times10^{-1}$ mol of Ru per 1 mol of (dimethylvinylgermoxy)heptasubstituted silsesquioxane of the formula 2.

4. The method, as claimed in claim 2, wherein the catalyst is used in an amount from $0.5\times10^{-2}$ to $5\times10^{31\ 2}$ mol of Ru per 1 mol of (dimethylvinylgermoxy)heptasubstituted silsesquioxane of the formula 2.

5. The method, as claimed in claim 2, wherein the catalyst is used in an amount of $2\times10^{-2}$ mol of Ru per 1 mol of (dimethylvinylgermoxy)heptasubstituted silsequioxane of the formula 2.

6. The method, as claimed in claim 2, wherein a copper(I) or (II) salt is additionally used as a cocatalyst in an amount of $10^{-1}$-10 mol of Cu per 1 mol of Ru.

7. The method, as claimed in claim 3, wherein a copper(I) or (II) salt is additionally used as a cocatalyst in an amount of $10^{-1}$-10 mol of Cu per 1 mol of Ru.

8. The method, as claimed in claim 4, wherein a copper(I) or (II) salt is additionally used as a cocatalyst in an amount of $10^{-1}$-10 mol of Cu per 1 mol of Ru.

9. The method, as claimed in claim 5, wherein a copper(I) or (II) salt is additionally used as a cocatalyst in an amount of $10^{-1}$-10 mol of Cu per 1 mol of Ru.

10. The method, as claimed in claim 6, wherein the copper (I) or (II) salt is used in an amount of 5 mol of Cu per 1 mol of Ru.

11. The method, as claimed in claim 7, wherein the copper (I) or (II) salt is used in an amount of 5 mol of Cu per 1 mol of Ru.

12. The method, as claimed in claim 8, wherein the copper (I) or (II) salt is used in an amount of 5 mol of Cu per 1 mol of Ru.

13. The method, as claimed in claim 9, wherein the copper (I) or (II) salt is used in an amount of 5 mol of Cu per 1 mol of Ru.

* * * * *